US006242000B1

(12) United States Patent
Armitage et al.

(10) Patent No.: US 6,242,000 B1
(45) Date of Patent: *Jun. 5, 2001

(54) COMPOSITION OF S–SODIUM IBUPROFEN

(75) Inventors: Bernard John Armitage; John Francis Lampard; Alan Smith, all of Nottinghamshire (GB)

(73) Assignee: The Boots Company PLC, Nottingham (GB)

( * ) Notice: Subject to any disclaimer, the term of this patent is extended or adjusted under 35 U.S.C. 154(b) by 0 days.

This patent is subject to a terminal disclaimer.

(21) Appl. No.: 08/942,717

(22) Filed: Oct. 2, 1997

Related U.S. Application Data

(62) Division of application No. 08/557,565, filed on Nov. 14, 1995, now Pat. No. 5,696,165, which is a division of application No. 08/137,092, filed on Oct. 26, 1993.

(30) Foreign Application Priority Data

May 13, 1991 (GB) ................................. 9110342
Jun. 5, 1991 (GB) ................................. 9112058

(51) Int. Cl.$^7$ ............................... A61K 9/14; A61K 9/20; A61K 9/46; A61K 9/48; A61K 31/19
(52) U.S. Cl. ......................... 424/464; 424/436; 424/443; 424/449; 424/451; 424/466; 424/489; 424/455; 514/786; 514/886; 514/937; 514/944; 514/969; 514/570
(58) Field of Search .................................. 424/464, 466, 424/489, 443, 449, 436, 451, 455

(56) References Cited

U.S. PATENT DOCUMENTS

| | | |
|---|---|---|
| 4,684,666 | 8/1987 | Haas . |
| 4,831,147 | 5/1989 | Russell . |
| 4,851,444 | 7/1989 | Sunshine et al. . |
| 4,859,704 | 8/1989 | Haas . |
| 4,861,797 | 8/1989 | Haas . |
| 4,865,770 | 9/1989 | Piselli . |
| 4,873,231 | 10/1989 | Smith . |
| 4,877,620 | 10/1989 | Loew et al. . |
| 4,931,587 | 6/1990 | Piselli . |
| 4,946,997 | 8/1990 | Larsen et al. . |
| 4,973,745 | 11/1990 | Blaschke et al. . |
| 4,980,375 | 12/1990 | Sunshine et al. . |
| 4,994,604 | 2/1991 | Tung et al. . |
| 5,015,764 | 5/1991 | Manimaran ..................... 562/401 |
| 5,100,918 | 3/1992 | Sunshine et al. . |
| 5,164,398 | 11/1992 | Sims et al. . |
| 5,189,208 | 2/1993 | Stahly ............................ 562/402 |
| 5,200,558 | 4/1993 | Kwan . |
| 5,220,053 | 6/1993 | Choudhury et al. ............ 562/401 |
| 5,235,095 | 8/1993 | Kadkhodayan et al. ........ 560/218 |
| 5,235,100 | 8/1993 | Choudhury et al. ............ 562/401 |
| 5,235,101 | 8/1993 | Patil et al. ...................... 562/401 |
| 5,248,213 | 9/1993 | Manimaran et al. . |
| 5,248,813 | 9/1993 | Manimaran et al. ............ 562/401 |
| 5,256,816 | 10/1993 | Murray et al. ................. 562/401 |
| 5,260,482 | 11/1993 | Pringle et al. ................. 562/401 |
| 5,278,337 | 1/1994 | Manimaran et al. ........... 562/401 |
| 5,302,751 | 4/1994 | Manimaran et al. ........... 562/401 |
| 5,696,165 | * 12/1997 | Armitage et al. ............... 514/570 |

FOREIGN PATENT DOCUMENTS

| | | |
|---|---|---|
| 55091/90 | 11/1990 | (AU) . |
| 55092/90 | 11/1990 | (AU) . |
| 3922441 | 1/1991 | (DE) . |
| 70714 | 1/1983 | (EP) . |
| 228164 | 7/1987 | (EP) . |
| 279519 | 8/1988 | (EP) . |
| 340663 | 11/1989 | (EP) . |
| 351353 | 1/1990 | (EP) . |
| 369228 | 5/1990 | (EP) . |
| 418043 | 3/1991 | (EP) . |
| 1573322 | of 1908 | (GB) . |
| 971700 | 9/1964 | (GB) . |
| 53-112837 | 10/1978 | (JP) . |

OTHER PUBLICATIONS

Brooks et al., *Journal of Chromatography*, vol. 99, pp. 541–551 (1974).

Maclean et al., *Am. Jour. of Cardiology*, vol. 41, p. 394 (1978).

Stratton et al., *Gynecologic Oncology*, 18, pp. 145–149 (1984).

Lee et al., "Liquid Chromatographic Determination and Plasma Concentration Profile of Optical Isomers of Ibuprofen in Humans", *J. Pharm. Sci.*, vol. 73, No. 11, 1542–1544 (1984).

Lee et al., "Stereoselective Disposition of Ibuprofen Enantiomers in Man", *Brit. J. Clin. Pharmac.*, 19, 669–674 (1985).

Collet, In Chiral Separations by HPLC. Krstulovic, A. M. Ed.; Ellis–Horwood Ltd. Chichester, 1989, Chapter 4.

Gabard et al., *Nouv. J. Chem.*, 1986, 10, 685.

Jacques et al. "Enantiomers, Racemates and Resolutions", Chapter 7, J. Wiley & Sons, NY, NY (1981) 423–434.

Collet et al. *Chem. Rev.*, 80(3), 215–230 (1980).

Collet, A. "Problems and Wonders of Chiral Molecules", *Simonyi*, M(Ed), Akademi Keado, Budapest (1990).

Lessel et al., XIIIth Int'l. Cong. of Rheumatology, Kyoto, 1973, pp.63–66.

Maclean et al., *Am. Jour. of Cardiology*, vol. 31, p. 394 (1978).

(List continued on next page.)

*Primary Examiner*—James M. Spear
(74) *Attorney, Agent, or Firm*—Arent Fox Kintner Plotkin & Kahn, PLLC

(57) ABSTRACT

The use of S(–)sodium 2-(4-isobutylphenyl)propionate (the sodium salt of S(+)-ibuprofen) in pharmaceutical compositions for the treatment of inflammation, pain and pyrexia is described. Preferred compositions comprise S(–)sodium 2-(4-isobutylphenyl)propionate dihydrate. Processes to prepare S(–)sodium 2-(4-isobutyl-phenyl)propionate and its use in a process to prepare S(+) 2-(4-isobutylphenyl) propionic acid of high enantiomeric purity are also described.

23 Claims, No Drawings

OTHER PUBLICATIONS

Kuna et al., *Clinical Research*, 428A.
Goldstein et al., *Jour. of Cardiovascular Pharmacology*, 2:399–409 (1980).
Koopmann et al. *Otolaryngology*, pp. 558–559 (1981).
Esquivel et al., *Thromb. Haemostas*, 48(1), pp. 87–90 (1982).
Colvin et al., *Am. J. Hosp. Pharm.*, 1983, 40:1025–1026.
Stratton et al., *Clin. Immunology & Immunopathology*, 28, pp. 170–176, (1983).
Stratton et al., *Gynecologic Oncology*, 18, 145–159 (1984).
Manson et al., *Circulation*, 1985, 72, III–85, No. 338.
Walter et al. *In vitro Cellular and Developmental Biology*, vol. 22, No. 9, pp. 535–541 (1986).
Sordelli et al., *Eur. J. Respir. Dis.*, 67, pp. 118–127 (1985).
Hubbard et al., *Circulatory Shock*, 26: 169–183 (1988).
Hubbard et al., *Procs. Soc. Exp. Biol. Med.*, 181(1), 183 (1986).
Stewart et al., *J. Trauma*, 28(7), 1093 (1988).
Eller et al., *Biopharmaceutics and Drug Disposition*, vol. 10, pp. 269–278, (1989).
Parsons et al., *Fasub. J.*, 3(4), No. 5452 (1989).
Johnston et al., *Prostaglandins, Leukotrienes and Essential Fatty Acids*, 43, pp. 119–132 (1991).
Manimaran et al. "Optical Purification of Profen Drugs", *Tetrahedron Assymetry*, vol. 4, No. 8, pp. 1949–1954 (1993).
Chemical Abstracts Search, 1993.
Jacques et al., *Enantiomers, Racemates and Resolutions*, Chapter 3, J. Wiley & Sons, NY, NY, pp. 167–213 (1981).
Kaiser et al, *Journal of Pharmaceutical Sciences*, vol. 65, No. 2, pp. 268–273 (1976).
Brooks et al, *Journal of Chromatography*, pp. 541–551 (1994).
Berge et al, *Journal of Pharmaceutical Sciences*, vol. 66, No. 1, pp. 1–2 (1977).

* cited by examiner

COMPOSITION OF S-SODIUM IBUPROFEN

This is a division of application Ser. No. 08/557,565, filed Nov. 14, 1995, U.S. Pat. No. 5,696,165 which is a divisional of Ser. No. 08/137,092 filed Oct. 26, 1993.

This invention relates to a salt of S(+)-ibuprofen, to its anti-inflammatory, anti-pyretic and analgesic activity, to pharmaceutical compositions containing the salt, to its use as an intermediate in a process to prepare S(+)-ibuprofen of high enantiomeric purity and to a novel form of the salt.

(±)-2-(4-Isobutylphenyl)propionic acid, ibuprofen, is a potent and well tolerated anti-inflammatory, analgesic and anti-pyretic compound. The racemic mixture consists of two enantiomers, namely S(+)-2-(4-isobutylphenyl)propionic acid or S(+)-ibuprofen and R(−)-2-(4-isobutylphenyl) propionic acid or R(−)-ibuprofen. It is known that S(+)-ibuprofen is the active agent and that R(−)-ibuprofen is partially converted into S(+)-ibuprofen in humans. The drug has been previously marketed as the racemic mixture, however, in certain circumstances it may be advantageous to administer S(+)-ibuprofen. Problems arise, however, when attempting to formulate S(+)-ibuprofen into pharmaceutical compositions due to its low melting point of 51° C.

DE 3922441 considers the formulation problems associated with the low melting point of S(+)-ibuprofen and proposes a solution to the problem by using the calcium salt of S(+)-ibuprofen on its own or in admixture with a compound selected from the group comprising the sodium-, potassium- or ammonium- S(+)-ibuprofen salt, ibuprofen or S-(+)-ibuprofen. It is disclosed that the pharmaceutical composition must contain the calcium salt as an essential component as alkali metal salts of S(+)-ibuprofen per se, for example the sodium salt, are too hygroscopic to allow satisfactory tabletting.

We have now prepared and characterised the sodium salt of S(+)-ibuprofen and surprisingly we have found that it possesses advantageous formulation properties. The sodium salt of S(+)-ibuprofen has a negative optical rotation of −4.3° and is thus correctly named as S(−)sodium 2-(4-isobutylphenyl)propionate.

The preparation of the sodium salt of S(+)-ibuprofen in anhydrous form for use as a base, as an alternative to the use of pyridine, in a process to racemise S(+)-ibuprofen, is described in U.S. Pat. No. 4,946,997. In this reference no details are given of the physical properties of the material obtained and there is no suggestion that the material is suitable for pharmaceutical use.

The administration of S(+)-ibuprofen as a solution in dilute sodium hydroxide to a normal subject in a volunteer study has been reported (Lee et al, J. Pharm Sci. Vol. 73, No.11, 1984, pp 1542–44). However, the taste of such a preparation would be unacceptable to the vast majority of patients.

The present invention provides pharmaceutical compositions comprising S(−)sodium 2-(4-isobutylphenyl) propionate having an enantiomeric purity of at least 90%, together with a pharmaceutically acceptable carrier, with the exception of (a) compositions consisting of a solution of S(−)sodium 2-(4-isobutylphenyl)propionate in water with no additional pharmaceutical excipient and (b) compositions comprising the calcium salt of S(+)-ibuprofen.

S(−)sodium 2-(4-isobutylphenyl)propionate possesses a number of formulation advantages over S(+)-ibuprofen. S(−)sodium 2-(4-isobutylphenyl)propionate may be easily compressed into tablets even on long compressing runs during which the temperature of the tablet tooling will rise. Under similar circumstances S(+)-ibuprofen would tend to stick and generally display poor flow characteristics. S(−) sodium 2-(4-isobutylphenyl)propionate may also be easily milled to the most appropriate particle size. These advantages would not be expected from consideration of the prior art (DE 3922441) referred to earlier.

The high melting point of S(−)sodium 2-(4-isobutylphenyl)propionate, 220–222° C., allows higher temperatures to be used in drying intermediates in formulation processes, for example granules, compared to the corresponding intermediates containing S(+)-ibuprofen. The high melting point also gives increased physical stability to final formulations containing S(−)sodium 2-(4-isobutylphenyl) propionate during storage for example in hot climates compared to final formulations containing S(+)-ibuprofen which may deteriorate when stored at temperatures close to the melting point of S(+)-ibuprofen.

S(−)sodium 2-(4-isobutylphenyl)propionate has a higher water solubility than S(+)-ibuprofen and is thus very useful in the formulation of pharmaceutical compositions containing water. Such compositions may be formulated to have a bright, clear, aesthetically-appealing appearance.

An additional formulation advantage is that S(−)sodium 2-(4-isobutylphenyl)propionate will resist esterification with excipients which contain a hydroxyl group for example mono-, di-, tri- or poly-hydric alcohols. For example this is a problem encountered when formulating S(+)-ibuprofen with liquid fill excipients, for example, esterified natural vegetable oils which may contain alcohols.

The enantiomeric purity of S(−)sodium 2-(4-isobutylphenyl)propionate used in the pharmaceutical compositions of the invention is in the range of 90–100%. Preferably the enantiomeric purity of the S(−)sodium 2-(4-isobutylphenyl)propionate used greater than 95%, more preferably the enantiomeric purity is greater than 98% and most preferably the enantiomeric purity is greater than 99%. In an especially preferred embodiment of the present invention the enantiomeric purity is greater than 99.5% e.g. greater than 99.9%. We have found that S(−)sodium 1-(4-isobutylphenyl)propionate can exist in the form of a stable dihydrate which is a novel and valuable compound for use in preparing pharmaceutical compositions. In the following detailed description of compositions of the invention the term S(−)sodium 2-(4-isobutylphenyl)propionate includes the anhydrous form and hydrated forms. Preferably the dihydrate is used.

S(−)sodium 2-(4-isobutylphenyl)propionate dihydrate may exist in more than one crystal form and the present invention includes each crystal form and mixtures thereof.

In therapeutic use, S(−)sodium 2-(4-isobutylphenyl) propionate may be administered orally, rectally, parenterally or topically, preferably orally or topically. Suitably the therapeutic compositions of the present invention may take the form of any of the known pharmaceutical compositions for oral, rectal, parenteral or topical administration. Pharmaceutically acceptable carriers suitable for use in such compositions are well known in the art of pharmacy. The compositions of the invention may contain 1–99% by weight of S(−)sodium 2-(4-isobutylphenyl)propionate. The compositions of the invention are generally prepared in unit dosage form. Preferably the unit dosage of S(−)sodium 2-(4-isobutylphenyl)propionate is in the range of 10–1200 mg in a precalculated amount to provide doses which are equivalent by weight to doses of for example 100 mg, 200 mg, 400 mg or 800 mg of S(+)-ibuprofen.

Solid compositions for oral administration are preferred compositions of the invention and there are known pharmaceutical forms for such administration, for example tablets and capsules. Suitably tablets may be prepared by mixing S(−)sodium 2-(4-isobutylphenyl)propionate with an inert diluent such as calcium phosphate in the presence of disintegrating agents, for example maize starch, and lubricating agents, for example magnesium stearate, and tableting the mixture by known methods. Such tablets may, if desired, be provided with enteric coatings by known methods, for example by the use of cellulose acetate phthalate. Similarly, capsules, for example hard or soft gelatin capsules, containing S(−)sodium 2-(4-isobutylphenyl)propionate with or without added excipients, may be prepared by conventional means and, if desired, provided with enteric coatings in a known manner. The tablets may be formulated in a manner known to those skilled in the art so as to give a controlled release of the compound of the present invention. Other compositions for oral administration include oily suspensions containing a compound of the present invention in a suitable vegetable oil, for example arachis oil.

Preferably, a solid composition comprises a) 10–99% S(−)sodium 2-(4-isobutylphenyl)propionate; b) 1–90% of a diluent and c) 0.1–10% of a lubricating agent, d) 0.1–15% of a disintegrating agent and optionally e) 0.1–15% of a binder. Optionally 0.1–10% of a flow aid may be added.

Preferably the diluent includes lactose, calcium phosphate, dextrin, microcrystalline cellulose, sucrose, starch, calcium sulphate or mixtures thereof. More preferably the diluent is lactose or calcium phosphate. Preferably the lubricating agent includes magnesium stearate, stearic acid, calcium stearate or mixtures thereof. More preferably the lubricating agent is magnesium stearate or stearic acid. Preferably the disintegrating agent includes microcrystalline cellulose, maize starch, sodium starch glycollate, low substituted hydroxypropyl cellulose, alginic acid or croscarmellose sodium or mixtures thereof. Preferably the binder includes polyvinyl pyrrolidone, gelatin, hydroxypropylmethyl cellulose, starch or mixtures thereof. More preferably the binder is polyvinylpyrrolidone. Suitable flow aids include talc and colloidal silicon dioxide. It will be appreciated by those skilled in the art that a particular excipient may perform more than one function for example maize starch may act as a diluent, a binder or as a disintegrating agent.

Controlled release forms of S(−)sodium 2-(4-isobutylphenyl)propionate include rapid release formulations such as soluble granules or melt filled fast release capsules, delayed release formulations such as tablets provided with enteric coatings, for example, of cellulose acetate phthalate and, in particular, sustained release formulations. Numerous types of sustained release formulations are known to those skilled in the art. Typically, S(−)sodium 2-(4-isobutylphenyl)propionate may be encapsulated within a release retarding coating, for example, a copolymer of cellulose ether and acrylate, or may be bound to small particles such as, for example, ion exchange resin beads. Alternatively, S(−)sodium 2-(4-isobutylphenyl)propionate may be incorporated into a matrix containing a release retarding agent such as a hydrophilic gum e.g. xanthan gum, a cellulose derivative e.g. hydroxypropyl methylcellulose, or a polysaccharide, wax or plastics material. Such techniques may provide sustained blood levels of S(+)-ibuprofen by controlling, for example, erosion, swelling, disintegration and dissolution of the composition within the gastrointestinal tract.

Liquid fill compositions for example viscous liquid fills, liquid paste fills or thixotropic liquid fills are also suitable for oral administration. Melt filled compositions may be obtained by mixing S(−)sodium 2-(4-isobutylphenyl) propionate with certain esters of natural vegetable oil fatty acids, for example, the Gelucire (Trademark) range available from Gattefosse to provide a variety of release rates. Suitably a melt-filled capsule comprises a) 10–80% S(−) sodium 2-(4-isobutylphenyl)propionate and b) 20–90% of a fatty acid ester excipient which comprises one or more polyol esters and triglycerides of natural vegetable oil fatty acids.

Solid compositions designed to effervesce when added to water to form an effervescent solution or suspension are also suitable for oral administration. Suitably an effervescent composition comprises a) 1–50% of S(−)sodium 2-(4-isobutylphenyl)propionate and b) a pharmaceutically acceptable effervescent couple. Such a composition may be presented in the form of tablets or granules. Although S(−)sodium 2-(4-isobutylphenyl)proionate may have advantageous organoleptic properties compared to the sodium salt of racemic ibuprofen preferably the effervescent compositions additionally comprise a taste masking component for example a sweetener, a flavouring agent, arginine, sodium carbonate or sodium bicarbonate.

Solid non-effervescent compositions are preferred compositions of the present invention. Preferably such compositions comprise S(−)sodium 2-(4-isobutylphenyl) propionate as the dihydrate.

Preferably oral liquid compositions comprise a) 0.1–10% S(−)sodium 2-(4-isobutylphenyl)propionate b) 1–50% of a diluent c) water to 100%. Optionally the composition may contain alcohol and/or include a preservative. Suitable diluents include sweetening agents for example sorbitol, xylitol, sucrose, or LYCASIN® (registered trademark of Roquette). Flavourings or other taste-masking agents known to those skilled in the art for example saccharin, sodium saccharin may be added. The use of S(−)sodium 2-(4-isobutylphenyl) propionate in aqueous liquid compositions is particularly advantageous as it provides clear, homogeneous, bright formulations which are aesthetically appealing to the consumer in addition to the beneficial pharmacological effect provided.

Compositions for topical administration are also preferred compositions of the invention. Suitably the S(−) sodium 2-(4-isobutylphenyl)propionate may be dispersed in a pharmaceutically acceptable cream, ointment or gel. A suitable cream may be prepared by incorporating S(−) sodium 2-(4-isobutylphenyl)propionate in a topical vehicle such as petrolatum and/or light liquid paraffin, dispersed in an aqueous medium using surfactants. An ointment may be prepared by mixing S(−)sodium 2-(4-isobutylphenyl) propionate with a topical vehicle such as a mineral oil, petrolatum and/or a wax e.g. paraffin wax or beeswax. A gel may be prepared by mixing S(−)sodium 2-(4-isobutylphenyl)propionate with a topical vehicle comprising a gelling agent e.g. basified Carbomer BP, in the presence of water.

Suitable topically administrable compositions may also comprise a matrix in which the pharmaceutically active compounds of the present invention are dispersed so that the compounds are held in contact with the skin in order to administer the compounds transdermally for example in a patch or poultice. A suitable transdermal composition may be prepared by mixing S(−)sodium 2-(4-isobutylphenyl) propionate with a topical vehicle, such as described above, together with a potential transdermal accelerant such as dimethyl sulphoxide, propylene glycol or peppermint oil.

Semi-solid compositions are preferred for topical use for example compositions in the form of a cream, an ointment or a gel. Suitable gels comprise a) 1–15% S(−)sodium 2-(4-isobutylphenyl)propionate; b) 1–20% of a gelling agent c) 0.01–10% of a preservative and d) water to 100%. Preferably the gelling agent comprises 0.1–10% of a carbomer and a neutralising agent. It is a particular advantage of the present invention that as a result of the high water solubility of S(−)sodium 2-(4-isobutylphenyl)propionate clear gels are obtained which have an acceptable cosmetic appearance and texture in addition to their pharmacological actvity.

A suitable cream comprises a) 1–15% S(−)sodium 2-(4-isobutylphenyl)propionate; b) 5–40% of an oily phase; c) 5–15% of an emulsifier; d) 30–85% of water. Suitable oily phases comprise petrolatum and/or light liquid paraffin.

Alternatively, S(−)sodium 2-(4-isobutylphenyl)propionate may be distributed in a base comprising a) 10–40% of a self-emulsifying base b) 60–90% of water to form a cream. LABRAFILL and GELOT (both tradenames of Gattefosse) are examples of self-emulsifying bases.

A suitable ointment comprises a) 1–15% S(−)sodium 2-(4-isobutylphenyl)propionate and b) a topical vehicle to 100%. Suitable topical vehicles include mineral oil, petrolatum and/or a wax.

Compositions of the invention suitable for rectal administration are known pharmaceutical forms for such administration, for example suppositories with polyethylene glycol bases or semi-synthetic glycerides. Preferably the composition in the form of a suppository comprises 10–30% S(−)sodium 2-(4-isobutylphenyl)propionate and 70–90% of a carrier wherein the carrier is selected from a base which comprises polyethylene glycol or a semi-synthetic glyceride.

Compositions of the invention suitable for parenteral administration are known pharmaceutical forms for such administration, for example sterile suspensions or sterile solutions in a suitable solvent.

In some formulations it may be beneficial to use S(−) sodium 2-(4-isobutylphenyl)propionate in the form of particles of very small size, for example as obtained by fluid energy milling.

In the compositions of the present invention the S(−) sodium 2-(4-isobutylphenyl)propionate may, if desired, be associated with other compatible pharmacologically active ingredients and/or enhancing agents. Thus, for example, S(−)sodium 2-(4-isobutylphenyl)propionate may be combined with any ingredient commonly used in a cough or cold remedy, for example, an antihistamine, caffeine or another xanthine derivative, a cough suppressant, a decongestant, an expectorant, a muscle relaxant, or combinations thereof.

Suitable antihistamines which are preferably nonsedating include acrivastine, astemizole, azatadine, azelastine, bromodiphenhyrdramine, brompheniramine, carbinoxamine, cetirizine, chlorpheniramine, cyproheptadine, dexbrompheniramine, dexchlorpheniramine, diphenhydramine, ebastine, ketotifen, lodoxamide, loratidine, levocubastine, mequitazine, oxatomide, phenindamine, phenyltoloxamine, pyrilamine, setastine, tazifylline, temelastine, terfenadine, tripelennamine or triprolidine. Suitable cough suppressants include caramiphen, codeine or dextromethorphan. Suitable decongestants include pseudoephedrine, phenylpropanolamine and phenylephrine. Suitable expectorants include guaifensin, potassium citrate, potassium guaiacolsulphonate, potassium sulphate and terpin hydrate.

S(−)sodium 2-(4-isobutylphenyl)propionate is an anti-inflammatory, analgesic and anti-pyretic agent. It is, therefore, indicated for use in the treatment of rheumatoid arthritis, osteoarthritis, ankylosing spondylitis, seronegative arthropathies, periarticular disorders and soft tissue injuries. S(−)sodium 2-(4-isobutylphenyl)propionate may also be used in the treatment of postoperative pain, postpartum pain, dental pain, dysmenorrhoea, headache, musculoskeletal pain or the pain or discomfort associated with the following: respiratory infections, colds or influenza, gout or morning stiffness.

In another aspect the present invention provides a pharmaceutical composition comprising S(−)sodium 2-(4-isobutylphenyl)propionate having an enantiomeric purity of at least 90% together with a pharmaceutically acceptable carrier for use in the treatment of inflammation, pain and pyrexia. Preferably the S(−)sodium 2-(4-isobutylphenyl)propionate in present as the dihydrate.

In a further aspect the present invention provides the use of a pharmaceutical composition comprising S(−)sodium 2-(4-isobutylphenyl)propionate having an enantiomeric purity of at least 90% together with a pharmaceutically acceptable carrier for the manufacture of a medicament for use as an antiinflammatory, analgesic and anti-pyretic agent. Preferably the S(−)sodium 2-(4-isobutylphenyl)propionate in present as the dihydrate.

It will be appreciated that the present invention provides a method of treating inflammation, pain and pyrexia by administration of a pharmaceutical composition comprising S(−)sodium 2-(4-isobutylphenyl)propionate having an enantiomeric purity of at least 90% together with a pharmaceutically acceptable carrier to a mammal, e.g. a human, in need thereof. Preferably the S(−)sodium 2-(4-isobutylphenyl)propionate in present as the dihydrate.

S(−)sodium 2-(4-isobutylphenyl)propionate may be absorbed more quickly from the gastrointestinal tract in humans than S(+)-ibuprofen thus giving therapeutically acceptable plasma levels in a shorter period of time. This effect offers the possibility of eliciting an onset—hastened and/or enhanced therapeutic response, by use of S(−)sodium 2-(4-isobutylphenyl)propionate compared to S(+)-ibuprofen, which is especially important in cases where analgesia is required, for example, in headache or dental pain. Thus the present invention includes a method of eliciting an onset-hastened and/or enhanced analgesic response compared to the use of an equivalent dose of S(+)-ibuprofen in a mammal, e.g. a human, comprising the administration of S(−)sodium 2-(4-isobutylphenyl)propionate to a mammal in need thereof.

This surprising effect occurs not only when S(−)sodium 2-(4-isobutylphenyl)propionate is administered in solution but also when administered in other formulations, for example, solid formulations for oral use (for example tablets or capsules) or suppositories.

In another aspect the present invention provides a method of preparing a pharmaceutical composition comprising S(−)-sodium 2-(4-isobutylphenyl)propionate together with a diluent or carrier characterised in that S(−)sodium 2-(4-isobutylphenyl)propionate dihydrate is used as the source of S(−)sodium 2-(4-isobutylphenyl)propionate.

In a further aspect the present invention provides a process to prepare a pharmaceutical composition comprising S(−)sodium 2-(4-isobutylphenyl)propionate having an enantiomeric purity of at least 90% together with a pharmaceutically acceptable carrier comprising combining S(−)sodium 2-(4-isobutylphenyl)propionate having an enantiomeric purity of at least 90% in solid form with a pharmaceutically acceptable carrier and formulating into a dosage form.

A preferred process for preparing a solid composition in tablet form comprises combining 10–90% of S(−)sodium 2-(4-isobutylphenyl)propionate having an enantiomeric purity of at least 90% with 1–90% of a diluent, optionally adding other pharmaceutically acceptable excipients selected from lubricating agents, disintegrating agents, binders, flow aids, oils, fats and waxes, mixing the ingredients with one another to form a uniform mixture, and compressing the mixture thus obtained to form tablets which may be optionally coated with a film coat or a sugar-coat.

Processes for the preparation of S(−)sodium 2-(4-isobutylphenyl)propionate will now be described. These processes form another aspect of the present invention. In the following description of these processes the term S(−) sodium 2-(4-isobutylphenyl)propionate includes the anhydrous form and hydrated forms for example the dihydrate.

S(−)sodium 2-(4-isobutylphenyl)propionate may be prepared by neutralising S(+)-2-(4-isobutylphenyl) propionic acid with a sodium-containing base. It would be expected that in order to prepare S(−)sodium 2-(4-isobutylphenyl) propionate in an enantiomerically pure form, for example greater than 90%, then the S(+)-2-(4-isobutylphenyl) propionic acid employed would be required to be greater than 90%. While this procedure may be used, it is time-consuming and costly to prepare S(+)-2-(4-isobutylphenyl) propionic acid of greater than 90% enantiomeric purity. Typically racemic ibuprofen is resolved using S(−)-1-phenylethylamine as described in the Journal of Pharmaceutical Sciences, 1976, page 26. The intermediate S(−)-1-phenylethylammonium S(+)-2-(4-isobutylphenyl) propionate salt requires several recrystallisations to raise the enantiomeric purity of the S(+)-ibuprofen produced, after hydrolysis of the salt, to above 90%. The amine employed is expensive and in theory the yield of S(+)-ibuprofen obtained cannot exceed 50%. The unwanted R(−)-ibuprofen may be racemised and the resolution procedure repeated to produce more S(+)-ibuprofen but overall the whole process is costly in terms of manpower, materials and plant equipment.

It is known that ibuprofen crystallises as a racemic compound rather than a mixture of enantiomers and that consequently preferential crystallisation is not an efficient process for the removal of small amounts of R(−)-ibuprofen from a sample of S(+)-ibuprofen.

Unexpectedly in preparing solid S(−)sodium 2-(4-isobutylphenyl)propionate we have discovered that this salt may be purified enantiomerically by crystallisation and that this surprising property may be utilised industrially to provide a simple, efficient and very cheap process to prepare S(−)sodium 2-(4-isobutylphenyl)propionate of high enantiomeric purity and to provide a process to prepare S(+)-ibuprofen of high enantiomeric purity. The process may be adapted to provide. R(+)sodium 2-(4-isobutylphenyl) propionate of high enantiomeric purity and optionally to prepare R(−)-ibuprofen of high enantiomeric purity.

Accordingly, the present invention provides a process for preparing a sodium salt of a desired enantiomer of 2-(4-isobutylphenyl)propionic acid said sodium salt having an enantiomeric purity of greater than 90% that is 90–100% comprising the steps of:

a) neutralising 2-(4-isobutylphenyl)propionic acid containing 50% or more of the desired enantiomer with a sodium-containing base in the presence of a solvent system;

b) crystallising to produce the solid sodium salt of the desired enantiomer; and c) separating said solid from the solvent system; and either d) recrystallising said solid or e) converting said solid into 2-(4-isobutylphenyl) propionic acid and repeating steps a, b and c.

This process is surprising since it is known in the art that pure enantiomers of arylpropionic acids may be racemised when heated in the presence of a base.

Suitably the 2-(4-isobutylphenyl)propionic acid used contains 70% or more of the desired enantiomer, preferably 80% or more of the desired enantiomer and more preferably 85% or more of the desired enantiomer.

In a more preferred embodiment the present invention provides a process for preparing S(−)sodium 2-(4-isobutylphenyl)propionate having an enantiomeric purity of greater than 90% comprising the steps of:

a) neutralising 2-(4-isobutylphenyl)propionic acid containing 85% or more of the S(+)-enantiomer with a sodium-containing base in the presence of a solvent system;

b) crystallising to produce solid S(−)sodium 2-(4-isobutylphenyl)propionate and c) separating said solid from the solvent system.

Optionally the S(−)sodium 2-(4-isobutylphenylpropionate may be recrystallised. Optionally, the S(−)sodium 2-(4-isobutylphenyl)propionate may be acidified to produce S(+)-2-(4-isobutylphenyl)propionic acid of higher enantiomeric purity than the acid used as starting material.

Preferably the process provides S(−)sodium 2-(4-isobutylphenyl)propionate having an enantiomeric purity of greater than 95%. More preferably the process provides S(−)sodium 2-(4-isobutylphenyl)propionate having an enantiomeric purity of greater than 98%. Most preferably the process provides S(−)sodium 2-(4-isobutylphenyl) propionate having an enantiomeric purity of greater than 99%. In an especially preferred process the enantiomeric purity is greater than 99.5% e.g. greater than 99.9%.

In a most preferred embodiment the present invention provides a process for preparing S(−)sodium 2-(4-isobutylphenyl)propionate having an enantiomeric of greater than 99% comprising the steps of:

a) neatralising 2-(4-isobutylphenyl)propionic acid containing 95% or more of the S(+)-enantiomer with a sodium-containing base in the presence of a solvent system;

b) crystallising to produce solid S(−)sodium 2-(4-isobutylphenyl)propionate and c) separating said solid from the solvent system.

2-(4-Isobutylphenyl)propionic acid containing 50% of a desired enantiomer i.e. racemic ibuprofen may be prepared by methods known to those skilled in the art. 2-(4-Isobutylphenyl)propionic acid containing more than 50% of a desired enantiomer for example 70%, 80%, 85%, 90%, 95% and 98% may be prepared by the partial resolution of racemic ibuprofen via salt formation with an optionally active amine for example S(−)-1-phenylethylamine followed by separation and hydrolysis as is well known in the art. Alternatively starting material for use in the process containing more than 50% of a desired enantiomer 2-(4-isobutylphenyl)propionic acid may be prepared by asymmetric synthesis using chemical techniques for example asymmetric hydrogenation, or biochemical techniques, for example stereoselective enzymatic ester hydrolysis.

The term neutralisation as used above means that substantially a molar equivalent of base is used within acceptable experimental error of around 10%. It will be appreciated by a person skilled in the art that the sodium salt of 2-(4-isobutylphenyl)propionic acid will give a pH value of greater than 7 in aqueous solution. In practice we have found that best results are achieved by neutralisation in the range 90–98% for example 96% of the calculated amount of 2-(4-isobutylphenyl)propionic acid and then measuring the pH of the solution to confirm that it is into the range of pH 8–9.9 prior to crystallisation. If necessary the pH may be adjusted to the required value by the addition of more acid or base. It will be appreciated that if the solution is heated at a pH greater than 10 for any length of time that there is a possibility of racemisation occurring.

The formation of the sodium salt of S(+)-2-(4-isobutylphenyl)propionic acid may be carried out in numerous ways. Typically the acid is reacted with an equivalent of a sodium-containing base in a solvent system. Suitable sodium-containing bases are sodium hydroxide, sodium carbonate, sodium bicarbonate, a sodium alkoxide, for example sodium methoxide or sodium ethoxide, sodium hydride or sodamide. Preferably the sodium-containing base is sodium hydroxide or a sodium alkoxide. Most preferably the sodium-containing base is sodium hydroxide.

The solvent system employed depends on the sodium-containing base used and may be a single solvent or a mixture of solvents. The solvent system may contain water when a hydrolytically-stable, sodium-containing base is used, for example sodium hydroxide, or the solvent system may be substantially anhydrous when a hydrolytically-unstable, sodium-containing base, for example a sodium alkoxide or sodium hydride, is used. The purpose of the solvent system is to allow contact between the acid and sodium-containing base to permit formation of the sodium salt of the acid and to provide a medium from which this salt will crystallise or precipitate. Any solvent system in which these purposes are achieved may be used.

Suitably the solvent system contains water. When the solvent system employed contains water in at least twice the stoichiometric amount of the 2-(4-isobutylphenyl)propionic acid used as the starting material then the S(−)sodium 2-(4-isobutylphenyl)propionate initially obtained is in the dihydrate form which may be dried by heating, optionally under vacuum to produce the anhydrous form. When the solvent system employed is anhydrous the initially formed S(−)sodium 2-(4-isobutylphenyl)propionate is anhydrous.

Suitable solvent systems for hydrolytically-stable, sodium-containing bases are water or mixtures of water and at least one water-miscible organic solvent for example acetone or a $C_{1-4}$ alcohol for example methanol, ethanol, propan-1-ol, propan-2-ol or butan-1-ol. Also suitable are mixtures of water and a partially water-miscible organic solvent for example methyl ethyl ketone. Preferably the solvent system comprises a mixture of water and acetone.

Alternatively the solvent system may comprise a mixture of water and a water-immiscible organic solvent in a two phase solvent system wherein the 2-(4-isobutylphenyl)propionic acid is dissolved in the organic phase and the base is dissolved in the aqueous phase. The mixture may be agitated for example by stirring or shaking to form the sodium salt of the acid in the aqueous layer. The sodium salt may be recovered from the aqueous layer, optionally after separating the two layers, by crystallisation optionally after the addition of a water miscible organic solvent, for example acetone. Suitable water-immiscible solvents are for example aliphatic hydrocarbons, aromatic hydrocarbons, halogenated hydrocarbons, ethers or esters. Preferably the water immiscible solvent is toluene.

When a hydrolytically-unstable, sodium-containing base is employed for example a sodium alkoxide such as sodium methoxide, a suitable solvent system comprises a substantially anhydrous inert organic solvent, for example toluene or methanol, which is compatible with the base employed.

Suitably the formation of the sodium salt is carried out at a temperature in the range of 0–150° C., although lower temperatures may be used, preferably in the range 5–120° C. and most preferably in the range 10–80° C. In a particularly preferred embodiment the formation of the sodium salt is carried out in the range from ambient temperature to 50° C. at atmospheric pressure.

Suitably the crystallisation of the sodium salt is carried out at a temperature in the range between the boiling point of the solvent system employed and the freezing point of the solvent system. Suitably the crystallisation may be carried out at a temperature in the range from −50° C. to +50° C., preferably in the range −20° C. to ambient temperature and most preferably from −10° C. to +10° C. at atmospheric pressure. It will be appreciated by those skilled in the art that the crystal size of the product obtained, may be varied by adjusting the crystallisation temperature, and by varying the rate of cooling.

In a preferred process according to the present invention S(+)2-(4-isobutylphenyl)propionic acid is converted into the sodium salt by reaction with sodium hydroxide in the presence of a solvent system comprising a mixture of water and acetone. Suitably the process is carried out in the range 0–80° C., preferably between 40° C. and 60° C. Suitably the volume ratio of acetone to water is in the range from 50:1 to 1:10 preferably the ratio is in the range 20:1 to 1:1 and most preferably in the range 15:1 to 2:1.

The sodium salt may be crystallised from the solvent system by methods for encouraging crystallisation known to those skilled in the art. For example the solvent system may be cooled, concentrated, seeded with the desired material or diluted with a solvent in which the sodium salt is less soluble or any combination of these methods may be employed. Preferably the solvent system is selected so that the sodium salt crystallises immediately after it is formed or on cooling of the solvent system.

The crystallised sodium salt may be separated from the solvent system by methods known to those skilled in the art for example by filtration or centrifugation.

In another aspect the present invention provides a process for preparing a sodium salt of a desired enantiomer of 2-(4-isobutylphenyl)propionic acid said sodium salt having an enantiomeric purity of greater than 90% comprising the steps of:

a) dissolving sodium 2-(4-isobutylphenyl)propionate containing 50% or more of the desired enantiomer in a solvent to form a saturated solution;

b) seeding said solution with the desired enantiomer of sodium 2-(4-isobutylphenyl)propionate;

c) cooling said solution in a controlled manner to cause crystallisation of the solid sodium salt;

d) separating said solid sodium salt from the solvent;

e) repeating steps a to d until the desired level of enantiomeric purity is achieved.

The crystallisation mother liquors which contain a higher proportion of the undesired enantiomer may be racemised by known methods, for example heating in the presence of a base e.g. sodium hydroxide, and the racemic salt obtained optionally by crystallisation or by evaporation, recycled by carrying out steps a) to e) above.

Suitably racemic sodium 2-(4-isobutylphenyl)propionate is used in the process. It may be prepared by hydrolysis of an ester of 2-(4-isobutylphenyl)propionic acid or by hydrolysis of 2-(4-isobutylphenyl)propionitrile or by hydrolysis of a 2-(4-isobutylphenyl) propionamide derivative or by other methods known to those skilled in the art.

Suitably any solvent or mixture of solvents, in which sodium 2-(4-isobutylphenyl)propionate is soluble and from which the salt may be recovered by crystallisation, may be employed. Suitably a mixture of water and a partially water miscible organic solvent for example methyl ethyl ketone may be used. Preferably, the solvent is a mixture of water and at least one water-miscible solvent selected from acetone or a $C_{1-4}$ alcohol for example methanol, ethanol, propan-1-ol, propan-2-ol or butan-1-ol. Most preferably the solvent comprises a mixture of water and acetone.

In a further aspect of the present invention the S(−)sodium 2-(4-isobutylphenyl)propionate obtained by any of the above processes may be acidified to produce S(+)-ibuprofen having an increased enantiomeric purity compared to that of the 2-(4-isobutylphenyl)-propionic acid used initially. This process is commercially extremely useful since S(+)-ibuprofen may be prepared by resolution of the racemic acid as described earlier or by asymmetric synthesis using chemical techniques, for example asymmetric hydrogenation, or biochemical techniques, for example stereoselective enzymatic ester hydrolysis. In such methods the final purification step is often a problem if the enantiomeric purity of the material obtained is not of the required standard. Previously an expensive resolution would have been required to upgrade the enantiomeric purity to an acceptable level, for example to greater than 99% purity. The process herein described provides a cheap and efficient method of increasing the enantiomeric purity of S(+)-ibuprofen to produce S(+)-ibuprofen of 99% or greater enantiomeric purity.

In a similar manner we have found that the enantiomeric purity of R(−)-ibuprofen may be increased by conversion into R(+)sodium 2-(4-isobutylphenyl)propionate using the same process.

As mentioned previously when the solvent system employed contains water in at least twice the stoichiometric amount of the 2-(4-isobutylphenyl)propionic acid used as the starting material, S(−)sodium 2-(4-isobutylphenyl) propionate dihydrate is produced, which is novel.

Accordingly, the present invention provides S(−)sodium 2-(4-isobutylphenyl)propionate dihydrate having an enantiomeric purity of at least 90%. Preferably the enantiomeric purity of the S(−)sodium 2-(4-isobutyl-phenyl)propionate dihydrate is greater than 95% (that is 95–100%), more preferably the enantiomeric purity is greater than 98% and most preferably the enantiomeric purity of the S(−)sodium 2-(4-isobutylphenyl)propionate dihydrate is greater than 99%. In an especially preferred embodiment of the present invention the enantiomeric purity of the S(−)sodium 2-(4-isobutylphenyl)propionate dihydrate is greater than 99.5% e.g. greater than 99.9%.

The solid dihydrate compound flows freely and does not absorb further water. A particularly preferred embodiment of the present invention comprises solid S(−)sodium 2-(4-isobutylphenyl)propionate dihydrate in which two molecules of water are present for each molecule of S(−)sodium 2-(4-isobutylphenyl)propionate.

In another aspect the present invention provides S(−)sodium 2-(4-isobutylphenyl)propionate for use in the treatment of inflammation, pain and pyrexia.

The invention is illustrated by the following non-limitative Examples.

The samples of S(+)-2-(4-isobutylphenyl)propionic acid used as the starting materials in the examples were prepared by resolving racemic ibuprofen using S(−)-1-phenylethylamine in a similar manner to that described in J. Pharm. Sci. 65 (1976) p.269–273. Acidification of the S(−)-1-phenylethylammonium S(+)-2-(4-isobutylphenyl) propionate salt initially produced gave S(+)-2-(4-isobutylphenyl)propionic acid of enantiomeric purity in the range 85–88%. Recrystallisation of the initially produced salt from propan-2-ol gave S(+)-2-(4-isobutylphenyl) propionic acid of enantiomeric purity in the range 95–99% after acidification.

The sample of R(−)-2-(4-isobutylphenyl)propionic acid used as a starting material was prepared by resolving racemic ibuprofen using R(+)-1-phenylethylamine in a similar manner to that described in J. Chromatography 99, (1974), p.541–551.

Enantiomeric Purity Determinations

The enantiomeric purity of samples of S(−)sodium 2-(4-isobutylphenyl)propionate was determined as follows. The S(−)sodium 2-(4-isobutylphenyl)propionate was acidified with 5 M hydrochloric acid and the mixture extracted with ether. The combined ether extracts were washed with water, dried and evaporated to give S(+)2-(4-isobutylphenyl) propionic acid.

This sample of S-(+)2-(4-isobutylphenyl)propionic acid was reacted with thionyl chloride and acetyl chloride to form S(+)-2-(4-isobutylphenyl)propionyl chloride which was then reacted with (−)-1-phenylethylamine to form N-(−)-1-phenylethyl-S(+)-2-(4-isobutylphenyl)propionamide. The amount of the diastereoisomeric amide formed from the R(−)-2-(4-isobutylphenyl)propionic present in each sample was determined using HPLC.

EXAMPLE 1

A solution of sodium hydroxide (6.4 g) in water (50 ml) was added over two minutes to a stirred solution of S(+)-2-(4-isobutylphenyl)propionic acid (41.2 g, enantiomeric purity 98.9%) in acetone (2 l) at ambient temperature. After standing for 30 minutes the precipitated salt was collected, washed with acetone and dried. The salt was taken up in warm water (45 ml) at 50–60° C. and stirred whilst acetone (300 ml) was added slowly over 5 minutes. The warm solution was decanted from the residue and whilst still warm was mixed with acetone (650 ml). The material which crystallised out on cooling was collected by filtration to give S(−)sodium 2-(4-isobutylphenyl)propionate dihydrate m.p. 220–222° C., $[\alpha]_D^{22}$=−4.3° (c 0.94). A sample converted back into S(+)-2-(4-isobutylphenyl)propionic acid as described above had $[\alpha]_D^{22}$=+58.7° (c 1.116). The enantiomeric purity was found to be at least 99.9%.

EXAMPLE 2

A mixture of S(+)-2-(4-isobutylphenyl)propionic acid (10.3 g, enantiomeric purity 95.9%), acetone (80 ml) and water (8 ml) was warmed to 50° C. A solution of sodium hydroxide (2.2 g) in water (4 ml) was added and the solution cooled. The solid formed was collected by filtration, washed with acetone and dried in air to give S(−)sodium 2-(4-isobutylphenyl)propionate dihydrate (yield 89%). Enantiomeric purity 99%.

EXAMPLE 3

A mixture of S(+)-2-(4-isobutylphenyl)propionic acid (20.6 g, enantiomeric purity 98.6%) and propan-2-ol (100 ml) was heated to 35° C. A solution of sodium hydroxide flake (4.0 g) in water (15 ml) was added. After cooling to 2° C., the salt which crystallised out was collected by filtration, washed with propan-2-ol (10 ml containing 10% water) then dried in air and finally under vacuum. The S(−)sodium 2-(4-isobutylphenyl)propionate obtained (yield 74%) was converted into S(+)-2-(4-isobutylphenyl)propionic acid and assayed as described previously. Enantiomeric purity 99.9%.

EXAMPLE 4

A mixture of S(+)-2-(4-isobutylphenyl)propionic acid (20.6 g, enantiomeric purity 98.6%), water (50 ml) and caustic soda flake (4.0 g) was stirred and heated at 60° C. until a solution was obtained. The solution was cooled to 5° C. and the S(−)sodium 2-(4-isobutylphenyl)propionate dihydrate which crystallised out was collected by filtration and dried under vacuum at 30° C. to give the anhydrous form (yield 53%). The salt was converted into S(+)-2-(4-isobutylphenyl)propionic acid and assayed as described in previously. Enantiomeric purity 99.9%.

EXAMPLE 5

A solution of sodium hydroxide (2.0 g) in water (7 ml) was added to a solution of S(+)-2-(4-isobutylphenyl) propionic acid (10.3 g, enantiomeric purity 98.6%) in acetone (60 ml). Immediate precipitation occurred. The mixture was cooled to 5° C. and the S(−)sodium 2-(4-isobutylphenyl)propionate dihydrate collected by filtration, washed with acetone (5 ml) then dried in air and finally under vacuum at 35° C. to give the anhydrous form (yield 83%). The salt was converted into S(+)-2-(4-isobutylphenyl) propionic acid and assayed as described previously. Enantiomeric purity 99.8%.

EXAMPLE 6

A mixture of S(+)-2-(4-isobutylphenyl)propionic acid (10.3 g, enantiomeric purity 88%), acetone (80 ml) and water (8 ml) was heated to 50° C. A solution of sodium hydroxide flake (2.5 g) in water (4 ml) was added and the mixture cooled to ambient temperature. The material which crystallised out was collected by filtration and washed with acetone to give S(−)sodium 2-(4-isobutylphenyl)propionate dihydrate (yield 53.7%). Enantiomeric purity 98.2%.

EXAMPLE 7

A mixture of S(+)-2-(4-isobutylphenyl)propionic acid (10.3 g, enantiomeric purity 98.6%), toluene (25 ml), water (7 ml) and sodium hydroxide (2.0 g) was heated to 80° C. More water (5 ml) was added. The mixture gradually separated into two layers. The lower aqueous layer was separated off and heated to 65° C. Acetone (80 ml) was added dropwise to the stirred warm aqueous layer and the mixture cooled to 5° C. More acetone (20 ml) was added and the mixture stirred at 2–5° C. for 1 hour. The S(−)sodium 2-(4-isobutyl phenyl)propionate dihydrate formed was collected by filtration, washed with acetone and dried in air to constant weight (yield 78%). The salt was converted into the acid and assayed as described previously. Enantiomeric purity 99.9%.

EXAMPLE 8

A solution of sodium methoxide formed by dissolving sodium (2.3 g) in methanol (30 ml) under reflux was added to a stirred solution of S(+)-2-(4-isobutylphenyl)propionic acid (20.6 g, enantiomeric purity 98.6%) in toluene (150 ml). After the addition more S(+)-2-(4-isobutylphenyl) propionic acid (0.8 g, optical purity 98.6%) was added to adjust the pH to 8. Methanol was removed by distillation until the still head temperature reached 100° C. and then the mixture was cooled to ambient temperature and filtered to give S(−)sodium 2-(4-isobutylphenyl)propionate (22.4 g, yield 94.5%). The salt was converted into the acid and assayed as described previously. Enantiomeric purity 99.3%.

EXAMPLE 9

Acetone (1080 l) was added to a solution of S(+)-2-(4-isobutylphenyl)propionic acid (211 kg, enantiomeric purity 98.2%) in toluene (850 kg) and the solution filtered. Caustic soda solution (80 kg, SG 1.5) was added over 30 minutes at 50–55° C. followed by water (77 l). The mixture was cooled to 5° C. and the precipitated solid was collected by filtration, washed with filtered acetone (2×200 l) and dried under vacuum at 50° C. to give S(−)sodium 2-(4-isobutylphenyl) propionate (84.4%, enantiomeric purity 99.95%).

EXAMPLE 10

Caustic soda solution (40 l, SG 1.5) and water (155 l) were added to a solution of S(+)-2-(4-isobutylphenyl) propionic acid (151 kg, enantiomeric purity 97.6%) in toluene (531 kg) and the mixture heated at 50° C. for 0.5 h with stirring. The aqueous phase was separated off and filtered. The organic phase was washed with water (50 l). The combined aqueous phases were heated to reflux and a mixture of residual toluene and water (120 l) was removed by distillation. The aqueous solution was cooled to below 40° C. and filtered acetone (1451 l) was added. The resulting slurry was heated at 55–60° C. for 0.5 h with stirring. The solution obtained was cooled to 1.5° C. and stirred at this temperature for 1 hour. The mixture was filtered and the residue washed with filtered acetone (2×200 l) and dried under vacuum at 50° C. to remove acetone to give S(−) sodium 2-(4-isobutylphenyl)propionate dihydrate (88.7% yield, enantiomeric purity 99.9%).

The acetone mother liquors (1570 kg) were treated with hydrochloric acid (5 l, SG 1.17) and water (300 l) and heated to 70° C. where acetone (1393 kg) was recovered by distillation. Water (300 l) was added to the residue and a water/acetone azeotrope (107 kg) was removed by distillation at 100° C. The aqueous residues were cooled to 57° C. and then hydrochloric acid (5 l, SG 1.17) and toluene (150 l) were added. The aqueous phase was removed by separation and the toluene phase was washed with water (300 l) at 60° C. The toluene phase containing crude S(+)-2-(4-isobutylphenyl)propionic acid was then reworked to produce more S(−) sodium 2-(4-isobutylphenyl)propionate.

EXAMPLE 11

Hydrochloric acid (76 l, SG 1.18) was added over 15 minutes to a mixture of S(−) sodium 2-(4-isobutylphenyl) propionate (203 kg, enantiomeric purity 99.4%), water (450 ml) and heptane (159 l). The aqueous phase was removed by separation and the heptane solution was washed with de-ionised water (2×200 l) at 30° C. The heptane solution was filtered and added to chilled heptane (159 l) over approximately 1.75 h. The mixture was kept at below −10° C. for 2 hours and the solid collected by filtration and dried under vacuum to give S(+)-2-(4-isobutylphenyl)propionic acid (121.3 kg, 76%, enantiomeric purity, 99.4%).

EXAMPLE 12

Tablets are prepared from the following ingredients:

|  | mg/tablet | % w/w |
|---|---|---|
| Core |  |  |
| S(−)sodium 2-(4-isobutylphenyl)-propionate dihydrate | 680 | 75.2 |
| methocel E50 | 12 | 1.3 |
| lactose spray dried | 137 | 15.2 |
| croscarmellose sodium | 33 | 3.7 |

-continued

|  | mg/tablet | % w/w |
|---|---|---|
| low substituted hydroxypropyl cellulose | 33 | 3.7 |
| magnesium stearate | 9 | 1.0 |
| Film Coat | | |
| hydroxypropylmethylcellulose | 20 | |
| white colouring agent | 6 | |
| talc | 4 | |

The drug is granulated with an aqueous solution of methocel. The dried granules are blended with the lactose, croscarmellose sodium, hydroxypropyl cellulose and magnesium stearate. The blend is compressed and then coated using an aqueous solution of the film-coating ingredients.

EXAMPLE 13

(Tablet)

|  | mg/tablet | % w/w |
|---|---|---|
| S(−)sodium 2-(4-isobutylphenyl) propionate dihydrate | 512 | 57.7 |
| tricalcium phosphate | 180 | 20.3 |
| microcrystalline cellulose | 60 | 6.8 |
| polyvinylpyrrolidone | 36 | 4.1 |
| croscarmellose sodium | 96 | 10.8 |
| magnesium stearate | 4 | 0.4 |

The drug, tricalcium phosphate and microcrystalline cellulose are granulated with a solution of polyvinylpyrrolidone in alcohol. The granules are dried and blended with croscarmellose sodium and magnesium stearate. The blend is compressed using capsule shaped tooling.

EXAMPLE 14

(Tablet)

|  | mg/tablet | % w/w |
|---|---|---|
| Core | | |
| S(−)sodium 2-(4-isobutylphenyl)-propionate dihydrate | 160 | 55.2 |
| maize starch | 128 | 44.2 |
| stearic acid | 1.6 | 0.6 |
| Sugar Coat | | |
| varnish layer | 1.3 | |
| acacia powdered | 1.3 | |
| refined sugar | 112 | |
| calcium sulphate dihydrate | 36 | |
| sodium carboxymethylcellulose | 0.8 | |
| colouring agent | 2.0 | |
| carnauba wax powder | 0.2 | |

The drug and a portion of the maize starch are granulated with a portion of the maize starch as a gel. The mixture is dried and blended with the remaining maize starch and is compressed. The cores are sugar-coated by serial application of varnish, build-up, smoothing and colouring syrups. The tablets are polished with carnauba wax.

EXAMPLE 15

(Melt Filled Capsules)

|  | mg/capsule | % w/w |
|---|---|---|
| S(−)sodium 2-(4-isobutylphenyl)-propionate dihydrate | 160 | 32.0 |
| GELUCIRE 44/14 (GELUCIRE is the trademark of Gattefosse) | 340 | 68.0 |

The drug is dispersed in the molten (GELUCIRE) and filled into hard gelatin capsules.

EXAMPLE 16

(Suppository)

|  | mg/suppository | % w/w |
|---|---|---|
| S(−)sodium 2-(4-isobutylphenyl) propionate dihydrate | 430 | 20.5 |
| WITEPSOL H 185 (WITEPSOL is the Trademark of Dynamit Nobel) | 1000 | 47.6 |
| WITEPSOL H 15 (WITEPSOL is the Trademark of Dynamit Nobel) | 670 | 31.9 |

The drug is dispersed in a mixture of the molten carriers. The mixture is poured into cavities to give a suppository of 2.1 g.

EXAMPLE 17

(Effervescent Tablet)

|  | mg/tablet | % w/w |
|---|---|---|
| S(−)sodium 2-(4-isobutylphenyl) propionate dihydrate | 128 | 11.3 |
| sodium bicarbonate | 800 | 70.7 |
| citric acid | 200 | 17.7 |
| sodium lauryl sulphate | 4 | 0.35 |

All ingredients are blended together and the resultant mix is compressed. A binding agent and/or a taste-masking component and/or flavouring may optionally be added.

EXAMPLE 18

(Effervescent Granule)

|  | mg/sachet | % w/w |
|---|---|---|
| S(−)sodium 2-(4-isobutylphenyl) propionate dihydrate | 512 | 16.5 |
| pulverised sugar | 1000 | 32.2 |
| malic acid | 350 | 11.3 |
| sodium saccharin | 25 | 0.8 |
| sodium bicarbonate | 476 | 15.3 |
| sodium carbonate | 143 | 4.6 |

-continued

|  | mg/sachet | % w/w |
|---|---|---|
| flavour | 100 | 3.2 |
| β-cyclodextrin | 500 | 16.1 |

All ingredients are dry blended together and are packed into foil sachets to give a dose of 400 mg of S(+)-ibuprofen.

EXAMPLE 19

(Cold Relief Tablet)

|  | mg/tablet | % w/w |
|---|---|---|
| Core |  |  |
| S(−)sodium 2-(4-isobutylphenyl) propionate dihydrate | 160 | 50.6 |
| pseudoephedrine hydrochloride | 30 | 2.9 |
| microcrystalline cellulose | 20 | 6.3 |
| croscarmellose sodium | 32 | 10.1 |
| polyvinylpyrrolidone | 12 | 3.8 |
| tricalcium phosphate | 60 | 19.0 |
| magnesium stearate | 2 | 0.6 |
| Film Coat |  |  |
| hydroxypropylmethylcellulose | 9 |  |
| talc | 1.6 |  |
| yellow colouring agent | 3.5 |  |

The sodium salt of S(+)-ibuprofen, tricalcium phosphate, microcrystalline cellulose and croscarmellose sodium are granulated with a solution of polyvinylpyrrolidone in alcohol. The dried granules are blended with the pseudoephedrine hydrochloride and magnesium stearate. The blend is compressed and the cores film-coated using an aqueous solution of the film-former.

EXAMPLE 20

(Topical Gel)

|  | % w/w |
|---|---|
| S(−)sodium 2-(4-isobutylphenyl)propionate dihydrate | 3.25 |
| Carbopol 980 NF (1) | 2.0 |
| polyethylene glycol 300 | 10.0 |
| 2-phenoxyethanol | 1.0 |
| Propylene glycol | 5.0 |
| Sodium hydroxide | 0.72 |
| Purified water | to 100 |

(1) CARBOPOL is the registered trademark of B. F. Goodrich.

The polyethylene glycol was mixed with about 25% of the required purified water and the Carbopol® dispersed in this mixture. About 56% of the required purified water was added with rapid stirring until the CARBOPOL® was well dispersed and appeared hydrated. The sodium hydroxide was dissolved in a minimum of purified water and added to the bulk with stirring. The S(+)-ibuprofen sodium salt dihydrate was dissolved in a mixture of phenoxyethanol, propylene glycol and remaining purified water and added to the Carbopol® gel with rapid stirring.

A clear gel of a viscosity suitable for use as a topical rub was produced. The inclusion of the free S(+)-ibuprofen acid in the above formulation gave an opaque product of a high viscosity not suitable for use as a topical rub.

The inclusion of a dose equivalent amount of the sodium salt of ibuprofen racemate in the formulation produced a totally unsatisfactory product that separated into a clear upper liquid and a cloudy viscous lower layer.

EXAMPLE 21

(Topical Gel)

|  | % |
|---|---|
| S(−)sodium 2-(4-isobutylphenyl)propionate dihydrate | 4.27 |
| polyethylene glycol 300 | 10 |
| carboxamer | 1 |
| 2-phenoxyethanol | 1 |
| triethanolamine | 1.35 |
| propylene glycol | 5 |
| purified water | to 100 |

Polyethylene glycol, phenoxyethanol and propylene glycol are added to a portion of water and mixed. The drug is added and then the carboxamer is dispersed. The carboxamer is gelled by addition of triethanolamine in the remaining water.

EXAMPLE 22

(Sustained Release Tablet)

|  | mg/tablet | % w/w |
|---|---|---|
| S(−)sodium 2-(4-isobutylphenyl) propionate dihydrate | 641 | 52.1 |
| xanthan gum | 227 | 18.45 |
| polyvinylpyrrolidone | 20 | 1.6 |
| stearic acid | 9 | 0.7 |
| colloidal silicon dioxide | 3 | 0.2 |

The sodium salt and a portion of the xanthan gum are granulated with a solution of the polyvinylpyrrolidone in isopropanol. The other ingredients and the remainder of the xanthan gum are blended into the mixture which is then compressed into tablets. The tablets may optionally be film-coated.

EXAMPLE 23

(Oral Liquid Low Strength)

|  | % w/w |
|---|---|
| S(−)-sodium 2-(4-isobutylphenyl)propionate dihydrate | 1.30 |
| LYCASIN ® 80/55 (1) | 40.0 |
| glycerin | 20.0 |
| domiphen bromide | 0.005 |
| alcohol 96% | 2.0 |
| purified water | to 100 |

(1) LYCASIN is the registered trademark of Roquette.

The LYCASIN® and glycerin were mixed together. The domiphen bromide was dissolved in the alcohol. The sodium salt was added to this alcoholic solution along with sufficient purified water to produce a solution. The aqueous alcoholic solution was added to the LYCASIN®/glycerin mixture and mixed well. Optional flavourings may be added to the above formulation.

S(+)-ibuprofen free acid, when included in the above formulation, gave a poor product with a significant proportion of the S(+)-ibuprofen floating on the surf ace of the product. The sodium salt gave a bright clear product.

EXAMPLE 24

(Oral Liquid (Low Strength))

|  | % |
|---|---|
| S(−)sodium 2-(4-isobutylphenyl)propionate dihydrate | 1.6 |
| xylitol | 35 |
| glycerin | 20 |
| xanthan gum | 0.35 |
| domiphen bromide | 0.005 |
| alcohol 96% | 2.0 |
| flavour | 0.1 |
| menthol | 0.01 |
| purified water | to 100 |

The xylitol is dissolved in half of the water, the xanthan gum is dispersed and allowed to hydrate, then the glycerin, the sodium salt of S-(+)-ibuprofen, the domiphen bromide and the saccharin sodium are added. The menthol and flavour are dissolved in alcohol and added to bulk. Water is added to make up the volume.

EXAMPLE 25

(Higher Strength Oral Liquid)

|  | % w/w |
|---|---|
| S(−)-sodium 2-(4-isobutylphenyl)propionate dihydrate | 2.6 |
| LYCASIN ® 80/55 (1) | 40.0 |
| glycerin | 20.0 |
| domiphen bromide | 0.005 |
| alcohol 96% | 2.0 |
| purified water | to 100 |

(1) LYCASIN is the registered trademark of Roquette.

The LYCASIN® and glycerin were mixed together and diluted with a suitable volume of water. The sodium salt was dispersed and dissolved in the mixture. The domiphen bromide was dissolved in the alcohol and this solution added slowly with stirring to the bulk. The formulation was made up to volume and mixed well. Optional flavourings may be added to the formulation.

The inclusion of S(+)-ibuprofen free acid in the above formulation gave an unsuitable product with the drug floating on the surface. The sodium salt produced a clear bright liquid.

EXAMPLE 26

(Oral Liquid (High Strength))

|  | % |
|---|---|
| S(−)sodium 2-(4-isobutylphenyl)propionate dihydrate | 3.2 |
| LYCASIN ® | 40 |
| glycerin | 20 |
| domiphen bromide | 0.005 |
| flavour | 0.2 |
| alcohol 96% | 2.0 |
| purified water | to 100 |

This is prepared in a similar manner to Example 24.

EXAMPLE 27

(Cold Relief Powder (Hot Drink))

|  | mg/sachet | % w/w |
|---|---|---|
| S(−)sodium 2-(4-isobutylphenyl) propionate dihydrate | 130 | 6.5 |
| β-cyclodextrin | 441 | 22.0 |
| pseudoephedrine hydrochloride | 30 | 1.5 |
| sodium saccharin | 20 | 1.0 |
| pulverised sugar | to 2000 | to 100 |

The powders were sieved through a 30 mesh sieve and blended together, then filled into sachets containing 2000 mg of powder. Optional flavourings may be added to the above mixture. On addition to hot water (70° C. or greater) a clear solution is produced which can be drunk by the patient.

In the same formulation base S-(+)-ibuprofen produced an unpalatable oily layer on the surface of the hot water.

EXAMPLE 28

(Cold Relief (Hot Water Drink))

|  | mg/sachet | % w/w |
|---|---|---|
| S(−)sodium 2-(4-isobutylphenyl) propionate dihydrate | 160 | 4.6 |
| pseudoephedrine hydrochloride | 30 | 0.9 |
| sodium saccharin | 20 | 0.6 |
| β-cyclodextrin | 1000 | 28.4 |
| pulverised sugar | 2000 | 57.0 |
| flavour | 300 | 8.6 |

The ingredients are dry blended together and packed into sachets.

In Examples 12–28, S(−)sodium 2(4-isobutylphenyl) propionate dihydrate may be replaced by the anhydrous form or other hydrated forms.

EXAMPLE 29

A solution of sodium hydroxide (0.65 g) in water (5 ml) was added to a stirred solution of R(−)-2-(4-isobutylphenyl) propionic acid (4.1 g) in acetone (200 ml). The mixture was stirred at ambient temperature for 30 minutes and the solid which crystallised was collected by filtration, washed with acetone and dried in air. This material was dissolved in hot water (6 ml) and stirred while acetone (200 ml) 1was added. The material which crystallised was collected by filtration and dried in air to give R(+)sodium 2-(4-isobutylphenyl) propionate dihydrate mp. 220–221° C., $[\alpha]^{22}_D$=+4.0° (c 0.934).

EXAMPLE 30

(Tablet)

|  | mg/tablet | % w/w |
|---|---|---|
| S(−)sodium 2-(4-isobutylphenyl)-propionate dihydrate | 769 | 69.9 |
| microcrystalline cellulose | 208 | 18.9 |
| croscarmellose sodium | 32 | 2.9 |
| lactose | 84 | 7.6 |
| colloidal silicon dioxide | 1 | 0.1 |
| magnesium stearate | 6 | 0.6 |

All the ingredients were blended together and the resultant mixture compressed into tablets (Tablet A).

The properties of the above tablets were compared with tablets containing the same excipients in the same amounts as indicated above, but replacing the S(−)sodium 2-(4-isobutylphenyl)propionate dihydrate with 600 mg S(+) 2-(4-isobutylphenyl)propionic acid (comparative Tablet A).

The pressure at which the tablets were compressed is indicated in the table below. The hardness of the resultant tablets was measured. The disintegration time was measured by the method of the British Pharmacopoeia 1980 and the dissolution time was measured using Apparatus 2 described in US Pharmacopeia XXII, section 711, p1578, with 900 ml of a phosphate buffer of the pH's indicated and a paddle speed of 50 revolutions per minute.

|  | Pressure (KN) | Hardness (Kp) | Disintegration Time | Dissolution Time (minutes) pH 7.2 $T_{50}$ | $T_{80}$ | pH 6.0 $T_{50}$ | $T_{80}$ |
|---|---|---|---|---|---|---|---|
| Tablet A | 11.0 | 4.72 | 10 m | 9.1 | 16.0 | — | — |
|  | 17.2 | 5.38 | — | — | — | 8.7 | 15.8 |
| Comparative Tablet A | 11.0 | 2.65 | 18 s | 6.3 | 19.0 | — | — |
|  | 16.4 | 3.15 | — | — | — | 34.1 | NA | s = seconds
m = minutes
NA = not attained
$T_{50}$ = time taken for 50% of active ingredient to be released from the tablet
$T_{80}$ = time taken for 80% of active ingredient to be released from the tablet From the results obtained it can be seen that Tablet A gave harder tablets than comparative Tablet A when compressed at the same pressure, and that Tablet A had a longer disintegration time and comparable dissolution at pH 7.2 but superior dissolution at pH 6.0.

EXAMPLE 31

(Tablet)

|  | mg/tablet | % w/w |
|---|---|---|
| S(−)sodium 2-(4-isobutylphenyl)-propionate dihydrate | 600 | 61.3 |
| tricalcium phosphate | 180 | 18.4 |
| microcrystalline cellulose | 60 | 6.1 |

-continued

|  | mg/tablet | % w/w |
|---|---|---|
| croscarmellose sodium | 96 | 9.8 |
| povidone | 36 | 3.7 |
| stearic acid | 6 | 0.6 |

The povidone was dissolved in a mixture of isopropanol and water (1:1 parts by volume). The S(−) sodium 2-(4-isobutylphenyl)propionate dihydrate was blended with the tricalcium phosphate, microcrystalline cellulose and croscarmellose sodium and then granulated with the solution of povidone. The granules were dried, sized, blended with the stearic acid and then compressed into tablets (Tablet B).

The properties of the above tablets were compared with tablets containing the same excipients in the same amounts as indicated above, but replacing the S(−)sodium 2-(4-isobutylphenyl)propionate dihydrate with 600 mg S(+) 2-(4-isobutylphenyl)propionic acid (comparative Tablet B).

The dissolution time of the resultant tablets was measured at pH 6 using the method described in Example 30.

|  | Dissolution time (minutes) $T_{50}$ | $T_{80}$ |
|---|---|---|
| Tablet B | 9.1 | 24.1 |
| Comparative Tablet B | 21.4 | NA |

NA = not attained
$T_{50}$ = time taken for 50% of active ingredient to be released
$T_{80}$ = time taken for 80% of active ingredient to be released It can be seen that Tablet B shows a superior dissolution performance compared with comparative Example B.

What is claimed is:
1. S(−)sodium 2-(4-isobutylphenyl)propionate dihydrate having an enantiomeric purity of at least 90%.
2. The compound according to claim 1 having an enantiomeric purity of at least 95%.

3. The compound according to claim 2 having an enantiomeric purity of at least 98%.

4. The compound according to claim 3 having an enantiomeric purity of at least 99.5%.

5. A method of treating inflammation, pain and/or pyrexia comprising administering a therapeutically effective amount of S(−)sodium 2-(4-isobutylphenyl)propionate dihydrate having an enantiomeric purity of at least 90% to a mammal in need thereof.

6. The method according to claim 1 wherein the enantiomeric purity is at least 98%.

7. The method according to claim 6 wherein the enantiomeric purity is at least 99.5%.

8. A pharmaceutical composition comprising
S(−)sodium 2-(4-isobutylphenyl)propionate dihydrate having an enantiomeric purity of at least 90%; and
a pharmaceutically acceptable carrier.

9. The composition according to claim 8 wherein S(−)sodium 2-(4-isobutylphenyl)propionate dihydrate has an enantiomeric purity of at least 98%.

10. The composition according to claim 8 comprising
(a) 10–99% w/w S(−)sodium 2-(4-isobutylphenyl)propionate dihydrate;
(b) 1–90% w/w of a diluent;
(c) 0.1–10% w/w of a lubricating agent; and
(d) 0.1–15% w/w of a disintegrating agent.

11. The composition according to claim 10 further comprising 0.1–15% w/w of a binder.

12. The composition according to claim 8 wherein the composition is in the form of a tablet or granules.

13. The composition according to claim 8 wherein the composition is in the form of a capsule, said capsule comprising
(a) 10–80% w/w S(−)sodium 2-(4-isobutylphenyl)propionate dihydrate; and
(b) 20–90% w/w of a fatty acid ester excipient which comprises at least one component selected from the group consisting of polyol esters and glycerides of natural vegetable oil fatty acids.

14. An effervescent composition according to claim 8 comprising (a) 1–30% w/w S(−)sodium 2-(4-isobutylphenyl) propionate dihydrate; and
(b) an effervescent couple.

15. The composition according to claim 14 wherein the composition is in the form of granules or a tablet.

16. The composition according to claim 8 comprising
(a) 0.1–10% S(−)sodium 2-(4-isobutylphenyl)propionate dihydrate;
(b) 1–50% of a diluent; and
(c) water to 100%;
wherein the composition is in a liquid form.

17. The composition according to claim 8, wherein the composition is in a semi-solid form of a cream, an ointment or a gel.

18. The composition according to claim 17 in the form of a gel comprising
(a) 1–15% w/w S(−)sodium 2-(4-isobutylphenyl) propionate dihydrate;
(b) 1–20% w/w of a gelling agent;
(c) 0.01–10% w/w of a preservative; and
(d) water to 100% w/w.

19. The composition according to claim 8 wherein the composition is in the form of a poultice or a patch for topical application.

20. The composition according to claim 8 in the form of a suppository comprising 10–30% w/w S(−)sodium 2-(4-isobutylphenyl)propionate dihydrate and 70–90% w/w of a carrier.

21. The composition according to claim 8 in the form of a unit dose.

22. The method of claim 5 for the treatment of a condition selected from the group consisting of postoperative pain, postpartum pain, dental pain, dysmenorrhoea, headache, musculoskeletal pain, pain or discomfort associated with respiratory infections, pain or discomfort associated with colds, pain or discomfort associated with influenza, pain or discomfort associated with gout, and pain or discomfort associated with morning stiffness.

23. The method of claim 22 for the treatment of dental pain, dysmenorrhoea, headache, colds, or influenza.

* * * * *